Feb. 4, 1958 E. S. BOERNER Plant Pat. 1,680
CHRYSANTHEMUM PLANT
Filed May 27, 1957
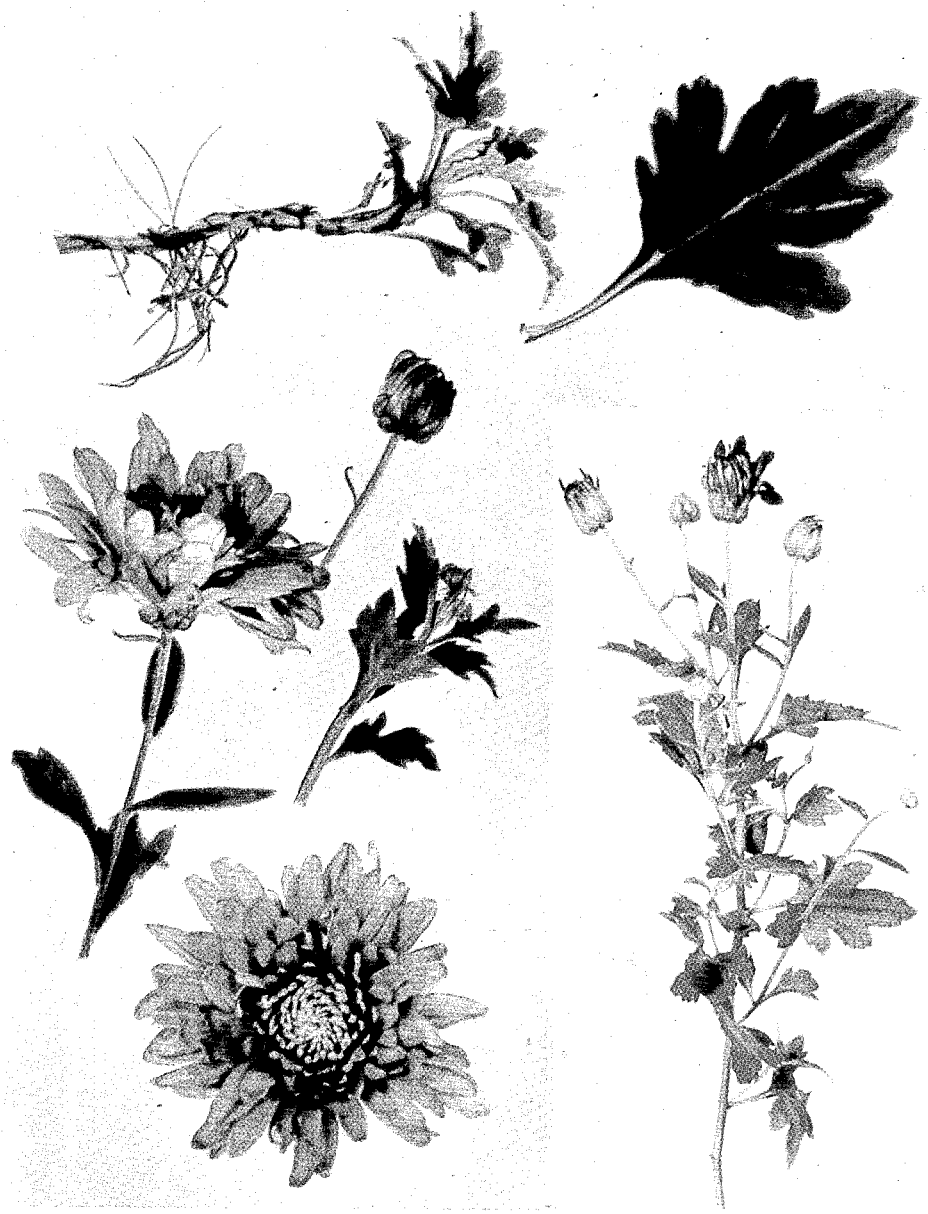
Inventor.
E. S. Boerner
By: Robb & Robb
Attorneys.

United States Patent Office

Plant Pat. 1,680
Patented Feb. 4, 1958

1,680

CHRYSANTHEMUM PLANT

Eugene S. Boerner, Newark, N. Y., assignor to Jackson & Perkins Company, Newark, N. Y., a corporation of New York Application May 27, 1957, Serial No. 661,985

1 Claim. (Cl. 47—60)

The present invention relates to a new and distinct variety of chrysanthemum plant of the decorative type, which was originated by me by crossing an unnamed and unpatented pink seedling derived from a cross of "W. P. Snyder" (unpatented) × "Kingbird" (Plant Patent No. 1,306) with the variety "Tanager" (Plant Patent No. 1,129).

The primary objective of this breeding was to produce a new chrysanthemum variety having the vigor and flower size of the parent variety "Kingbird," but having the flower color corresponding to that of the parent variety "Tanager." This objective was fully achieved, along with other improved features, as evidenced by the following characteristics which are outstanding in the new variety and which represent a unique combination in a chrysanthemum of this class:

(1) A vigorous and hardy growth;

(2) Attractive plant and flowers; and (3) A distinctive Carmine general color tonality of the flowers.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-while, as illustrative of the form and habit of growth of the plant.

The following is a detailed description of my new variety, with color terminology in accordance with Ridgway's Color Standards and Nomenclature, as based upon observations made from specimens grown outdoors at Newark, New York, in the late morning during the latter part of the mouth of September:

Parentage: An unnamed pink seedling derived from a cross of "W. P. Snyder" × "Kingbird" × "Tanager."

Classification: Decorative.

Growth: Upright; attains a height averaging about 21 inches.

Cold resistance: Plants are very winter hardy in northern New York; flowers are frost-resistant.

Blooming period: In the Newark, New York climatic area, blooming begins about September 27th and continues until frosts.

*Flower*

Bud:

*Color.*—When sepals first divide—Bordeaux, Plate 12. When petals begin to unfurl—Bordeaux, Plate 12, lightly overcast with Pomegranate Purple, Plate 12. When half-blown: Inside of petals—Carmine, Plate 1, with a slight overcast of Spectrum Red, Plate 1; reverse of petals—Ochraceous Salmon, Plate 15, lightly overcast with Eugenia Red, Plate 13.

*Penducle.*—Strong. Color—Light Cress Green, Plate 31.

Bloom:

*Size.*—Average about 5 inches.

*Stem.*—Strong.

*Form.*—Decorative.

*Petalage.*—Double.

*Color.*—Center of flower—Carmine, Plate 1. Outer petals—Spectrum Red, Plate 1, with slight overcast of Carmine, Plate 1. Base of petals—Picric Yellows, Plate 4. Inside of petals—Carmine, Plate 1. Reverse of petals—Pale Ochraceous Salmon, Plate 15, with center of petal lightly overcast with Acajou Red, Plate 13.

*Petals.*—Texture—stiff. Form—ovoid.

*Fragrance.*—Characteristic chrysanthemum.

*Plant*

Form: Upright; bushy.

Growth: Compact.

Foliage:

*Size.*—Small; leathery.

*Quantity.*—Normal.

*Color.*—Upper side—Forest Green, Plate 17. Reverse side—Light Elm Green, Plate 17.

*Texture.*—Leathery.

I claim:

A new and distinct variety of chrysanthemum plant of the decorative type, substantially as herein shown and described, characterized particularly as to novelty by its vigorous and hardy habits of growth, the attractiveness of its plant and flowers, and the distinctive Carmine general color tonality of its flowers.

No references cited.